(12) United States Patent
Wang et al.

(10) Patent No.: US 6,882,700 B2
(45) Date of Patent: Apr. 19, 2005

(54) TOMOSYNTHESIS X-RAY MAMMOGRAM SYSTEM AND METHOD WITH AUTOMATIC DRIVE SYSTEM

(75) Inventors: Yu Wang, Clifton Park, NY (US); Reinhold Franz Wirth, Ballston Spa, NY (US); James Pellegrino Alexander, Ballston Lake, NY (US)

(73) Assignee: General Electric Company, Niskayuna, NY (US)

( * ) Notice: Subject to any disclaimer, the term of this patent is extended or adjusted under 35 U.S.C. 154(b) by 403 days.

(21) Appl. No.: 10/063,357

(22) Filed: Apr. 15, 2002

(65) Prior Publication Data

US 2003/0194051 A1 Oct. 16, 2003

(51) Int. Cl.[7] .............................. A61B 6/04; H05G 1/02
(52) U.S. Cl. ............................ 378/37; 378/22; 378/27; 378/197
(58) Field of Search .............................. 378/21–27, 37, 378/146, 195–198

(56) References Cited

U.S. PATENT DOCUMENTS

| | | | |
|---|---|---|---|
| 3,971,950 A | | 7/1976 | Evans et al. |
| 4,407,163 A | | 10/1983 | Hundt et al. |
| 4,509,368 A | | 4/1985 | Whiting et al. |
| 4,543,959 A | | 10/1985 | Sepponen |
| 4,936,291 A | | 6/1990 | Forssmann et al. |
| 4,979,202 A | * | 12/1990 | Siczek et al. ............... 378/198 |
| 5,018,176 A | * | 5/1991 | Romeas et al. ............... 378/37 |
| 5,029,192 A | * | 7/1991 | Schwierz ..................... 378/4 |
| 5,361,767 A | | 11/1994 | Yukov |
| 5,386,447 A | * | 1/1995 | Siczek ......................... 378/37 |
| 5,474,072 A | | 12/1995 | Shmulewitz |
| 5,479,927 A | | 1/1996 | Shmulewitz |

(Continued)

OTHER PUBLICATIONS

A. Thomas Stavros et al.: "Solid Breast Nodules: Use of Sonography to Distinguish between Benign and Malignant Lesions," Radiology, Jul. 1995, pp. 123–134, vol. 196, No. 1, Englewood, CO.

Thomas M. Kolb et al.: "Occult Cancer in Women with Dense Breasts: Detection with Screening US–Diagnostic Yield and Tumor Characteristics," Radiology, Apr. 1998, pp. 191–199, vol. 207, No. 1.

Daniel B. Kopans et al.: "Development and Clinical Evaluation of Tomosynthesis for Digital Mammography; Technical and Cost Proposal," Clinical Translational Research Award, Department of Defense Breast Cancer Research Program, Nov. 19, 1997, pp. 1–54.

Nico Karssemeijer et al.: "Detection of Stellate Distortions in Mammograms," IEEE Transactions on Medical Imaging, Oct. 1996, pp. 611–619, vol. 15, No. 5, IEEE.

Ioanna Christoyianni et al.: "Fast Detection of Masses in Computer–Aided Mammography," IEEE Signal Processing Magazine, Jan. 2000, pp. 54–64.

(Continued)

*Primary Examiner*—Allen C. Ho
(74) *Attorney, Agent, or Firm*—Fletcher Yoder

(57) ABSTRACT

An imaging system includes an X-ray source adapted to move in an arc shaped path and a stationary electronic X-ray detector. The system also includes a track and a mechanical driving mechanism which is adapted to move the X-ray source in the arc shaped path. A tomosynthesis X-ray imaging method includes mechanically moving an X-ray source in a stepped motion on an arc shaped path around an object using a track and irradiating the object with an X-ray dose from the X-ray source located at a plurality of steps along the arc shaped path. The method also includes detecting the X-rays transmitted through the object with an electronic X-ray detector, and constructing a three dimensional image of the object from a signal output by the electronic X-ray detector.

34 Claims, 13 Drawing Sheets

U.S. PATENT DOCUMENTS

| | | | |
|---|---|---|---|
| 5,539,797 A | * | 7/1996 | Heidsieck et al. ............ 378/37 |
| 5,603,326 A | | 2/1997 | Richter |
| 5,630,426 A | | 5/1997 | Eggers et al. |
| 5,640,956 A | | 6/1997 | Getzinger et al. |
| 5,660,185 A | | 8/1997 | Shmulewitz et al. |
| 5,664,573 A | | 9/1997 | Shmulewitz |
| 5,735,264 A | | 4/1998 | Siczek et al. |
| 5,776,062 A | | 7/1998 | Nields |
| 5,803,082 A | | 9/1998 | Stapleton et al. |
| 5,810,742 A | | 9/1998 | Pearlman |
| 5,820,552 A | | 10/1998 | Crosby et al. |
| 5,828,774 A | | 10/1998 | Wang |
| 5,840,022 A | | 11/1998 | Richter |
| 5,851,180 A | | 12/1998 | Crosby et al. |
| 5,855,554 A | | 1/1999 | Schneider et al. |
| 5,872,828 A | | 2/1999 | Niklason et al. |
| 5,877,501 A | * | 3/1999 | Ivan et al. ............. 250/370.09 |
| 5,938,613 A | | 8/1999 | Shmulewitz |
| 5,983,123 A | | 11/1999 | Shmulewitz |
| 5,984,870 A | | 11/1999 | Giger et al. |
| 5,999,639 A | | 12/1999 | Rogers et al. |
| 6,180,943 B1 | | 1/2001 | Lange |
| 6,222,902 B1 | * | 4/2001 | Lin et al. ...................... 378/22 |
| 6,236,708 B1 | * | 5/2001 | Lin et al. ...................... 378/22 |
| 6,375,352 B1 | * | 4/2002 | Hewes et al. ................ 378/196 |
| 6,496,557 B1 | * | 12/2002 | Wilson et al. ................ 378/21 |
| 6,647,092 B1 | * | 11/2003 | Eberhard et al. ............. 378/65 |
| 6,751,285 B1 | * | 6/2004 | Eberhard et al. ............. 378/37 |
| 2003/0194050 A1 | * | 10/2003 | Eberhard et al. ............. 378/37 |

OTHER PUBLICATIONS

Celia Byrne et al.: "Mammographic Features and Breast Cancer Risk: Effects with Time, Age, and Menopause Status," Journal of the National Cancer Institute, Nov. 1, 1995, pp. 1622–1629, vol. 87, No. 21.

Matthew A. Kupinski et al.: "Feature Selection and Classifiers for the Computerized Detection of Mass Lesions in Digital Mammography," IEEE Int. Conf. On Neural Nets, 1997, pp. 2460–2463, IEEE.

Shuk–Mei Lai et al.: "On Techniques for Detecting Circumscribed Masses in Mammograms," IEEE Transactions on Medical Imaging, Dec. 1989, pp. 377–386, vol. 8, No. 4, IEEE.

Marios A. Gavrielides et al.: "Segmentation of Suspicious Clustered Microcalcifications in Mammograms," Med. Phys., Jan. 2000, pp. 13–22, vol. 27, No. 1, Am. Assoc. Phys. Med.

Wei Zhang et al.: "Optimally Weighted Wavelet Transform Based on Supervised Training for Detection of Microcalcifications in Digital Mammograms," Med. Phys. Jun. 1998, pp. 949–956, vol. 25, No. 6, Am. Assoc. Phys. Med.

Berkman Sahiner et al.: "Computerized Characterization of Masses on Mammograms: The Rubber Band Straightening Transform and Texture Analysis," Med. Phys. Apr. 1998, pp. 516–526, vol. 25, No. 4, Am. Assoc. Phys. Med.

Zhimin Huo et al.: "Computerized Analysis of Mammographic Parenchymal Patterns for Breast Cancer Risk Assessment: Feature Selection," Med. Phys., Jan. 2000, pp. 4–12, vol. 27, No. 1, Am. Assoc. Phys. Med.

Datong Wei et al.: "Classification of Mass and Normal Breast Tissue on Digital Mammograms: Multiresolution Texture Analysis," Med. Phys. Sep. 1995, pp. 1501–1513, vol. 22, No. 9, Am. Assoc. Phys. Med.

John J. Heine et al.: "Multiresolution Statistical Analysis of High–Resolution Digital Mammograms," IEEE Transactions on Medical Imaging, Oct. 1997, pp. 503–515, vol. 16, No. 5, IEEE.

Wouter J. H. Veldkamp et al.: Normalization of Local Contrast in Mammograms, IEEE Transaction on Medical Imaging, Jul. 2000, pp. 731–738, vol. 19, No. 7, IEEE.

Wei Qian et al.: "Tree Structured Wavelet Transform Segmentation of Microcalcifications in Digital Mammography," Med. Phys., Aug. 1995, pp. 1247–1254, vol. 22, No. 8, Am. Assoc. Phys. Med.

Highnam et al.: "Mammographic Image Analysis," 1999, pp. 39–53, 191–223, 228, Kluwer Academic Publishers.

Laura M. Yarusso et al.: "Application of Computer–Aided Diagnosis to Full–Field Digital Mammography," IWDM 2000, $5^{th}$ International Workshop on Digital Mammography, pp. 421–246, Medical Physics Publishing, Madison, Wisconsin.

Lihua Li et al.: "Hybrid Classification Method for False–Positive Reduction in CAD for Mass Detection," IWDM 2000, $5^{th}$ International Workshop on Digital Mammography, pp. 272–279, Medical Physics Publishing, Madison, Wisconsin.

Robert P. Velthuizen: "Computer Description of Mammographic Masses," IWDM 2000, $5^{th}$ International Workshop on Digital Mammography, pp. 395–401, Medical Physics Publishing, Madison, Wisconsin.

Armando Bazzani et al.: "Automatic Detection of Clustered Microcalcifications Using a Combined Method and an SVM Classifier," IWDM 2000, $5^{th}$ International Workshop on Digital Mammography, pp. 161–167, Medical Physics Publishing, Madison, Wisconsin.

Yoshihiro Hagihara et al.: "Accurate Detection of Microcalcifications on Mammograms by Improvement of Morphological Processing," IWDM 2000, $5^{th}$ International Workshop on Digital Mammography, pp. 193–197, Medical Physics Publishing, Madison, Wisconsin.

M. Lanyi: "Diagnosis and Differential Diagnosis of Microcalcifications," Ductal Carcinomas of Varying Histologic Types, pp. 44, 60, 61, 86, 95, 98–101, 110, 118–120, and 192, 1987, Springer–Verlag.

Daniel B. Kopans: "The Positive Predictive Value of Mammography," AJR, Mar. 1992, pp. 521–526, vol. 158, American Roentgen Ray Society.

* cited by examiner

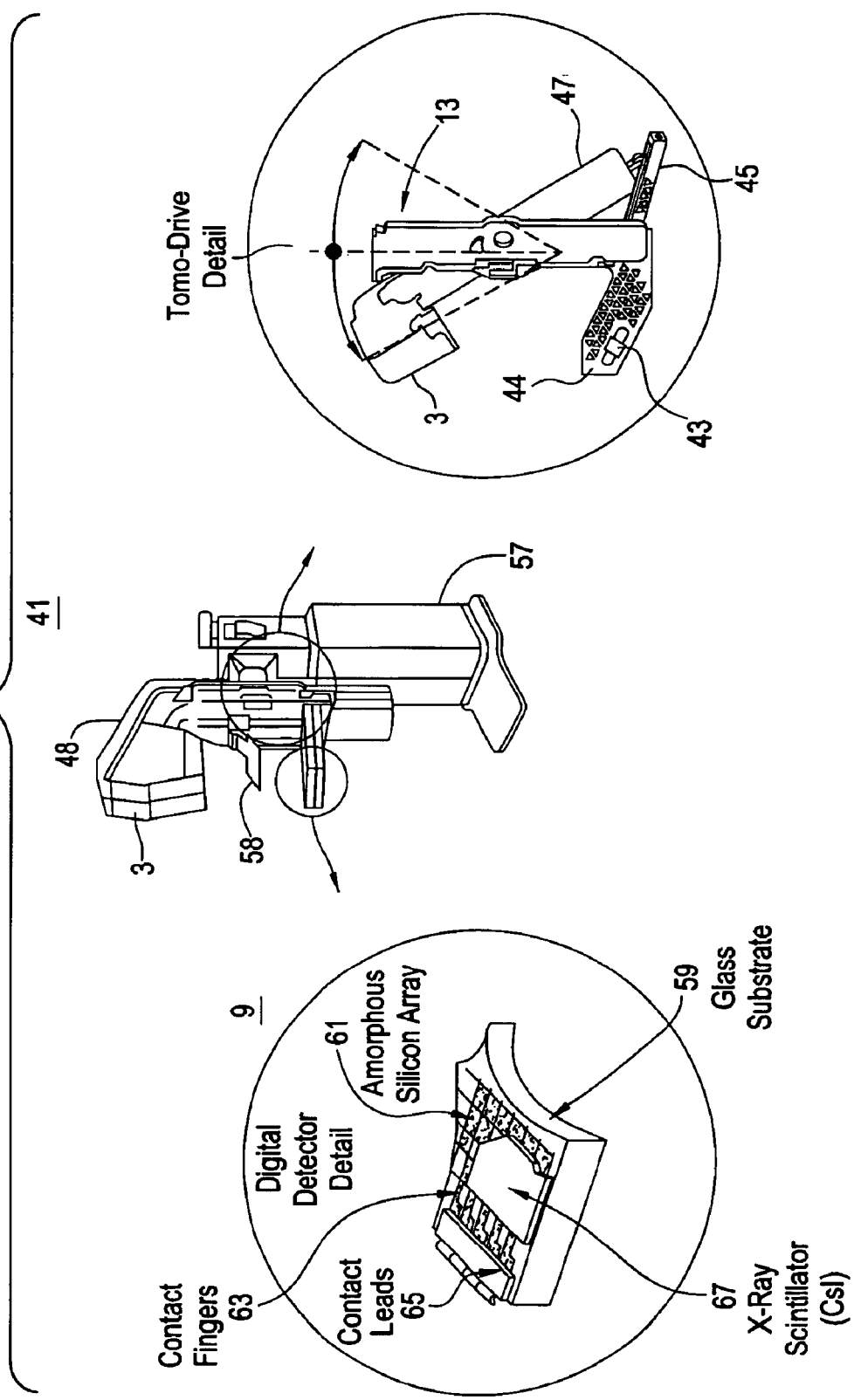

TOMOSYNTHESIS X-RAY MAMMOGRAM SYSTEM AND METHOD WITH AUTOMATIC DRIVE SYSTEM

FEDERAL RESEARCH STATEMENT

The U.S. Government may have certain rights in this invention pursuant to contract number DAMD 17-98-1-8309 awarded by the U.S. Army Medical Research and Materiel Command.

BACKGROUND OF THE INVENTION

The present invention relates generally to an imaging system, and more particularly to an X-ray mammogram tomosynthesis system.

Conventional X-ray mammography imaging systems utilize an X-ray source mounted on a supporting frame. The frame is manually rotated by the system operator to a place the X-ray source into desired position adjacent to a patient's breast. The X-ray source emits a first shot of X-rays through the patient's breast and an image is captured on a first an X-ray sensitive film positioned on the opposite side of the patient's breast. The frame is then manually rotated into another position by the operator and a second X-ray sensitive film is exposed by a second shot of X-rays. This procedure can be repeated several times to generate several images on different films. The images on the X-ray sensitive films may then be evaluated by a physician and/or digitized and evaluated by a computer. However, such a system produces a two dimensional image of the patient's breast, which provides insufficient information about the presence of tumors and calcification and often leads to false positive readings.

U.S. Pat. No 5,872,828 discloses a tomosynthesis system for breast imaging. This system produces a three dimensional image of the breast being imaged. The tomosynthesis system contains an X-ray source which moves in an arc shaped path over the breast that is being imaged, a stationary digital X-ray detector and an image processor. The detector is mounted on a stationary portion of a support structure. The X-ray source is mounted on a movable portion of the support structure. The movable portion of the support structure is an arm whose lower end is rotatably attached to the stationary support structure at a pivot point, and whose upper end supports the X-ray source.

However, this tomosynthesis system suffers from several disadvantages. First, the X-ray source is subject to a high amount of vibration because it is mounted to the free, upper end of a rotating arm, while the arm is supported only at the pivot point at its lower end. The vibration of the X-ray source distorts the image. Second, this system requires a high amount of driving power to move the X-ray source. The high driving power is required because torque is applied to the fixed, lower end of the arm, while the heavy X-ray source is mounted to the free, upper end of the arm.

BRIEF SUMMARY OF INVENTION

In accordance with one preferred aspect of the present invention, there is an imaging system, comprising an X-ray source adapted to move in an arc shaped path, a stationary electronic X-ray detector, a track, and a mechanical driving mechanism which is adapted to move the X-ray source in the arc shaped path.

In accordance with another preferred aspect of the present invention there is provided a tomosynthesis X-ray mammography imaging system, comprising an X-ray source adapted to move in an arc shaped path, an arc shaped track provided to allow the X-ray source to move in the arc shaped path, a stationary electronic X-ray detector positioned opposite to the X-ray source, and a mechanical driving mechanism which is adapted to move the X-ray source in the arc shaped path.

In accordance with another preferred aspect of the present invention, there is provided a tomosynthesis X-ray mammography imaging system, comprising an X-ray source mounted onto an upper portion of a first arm, a second arm having a first side and a second side and a stationary electronic X-ray detector mounted facing the X-ray source to a first side of the second arm such that an imaging volume is formed above the electronic X-ray detector. The system also comprises a shaft rotatably connecting a middle portion of the first arm to a middle portion of a second side of the second arm, a linear motion track adapted to move relative to the second arm, and a mechanical driving mechanism which is adapted to move a lower portion of the first arm along the linear motion track such that the X-ray source moves in an arc shaped path.

In accordance with another preferred aspect of the present invention, there is provided a tomosynthesis X-ray mammography imaging system, comprising a first means for irradiating a patient's breast with an X-ray dose at a plurality of steps along an arc shaped path, a second means for mechanically moving the first means in a stepped motion on the arc shaped path around the patient's breast, a third means for detecting the X-rays transmitted through the patient's breast, and a fourth means for constructing a three dimensional image of the patient's breast from a signal output by the third means.

In accordance with another preferred aspect of the present invention, there is provided a tomosynthesis X-ray imaging method, comprising mechanically moving an X-ray source in a stepped motion on an arc shaped path around an object using a track, irradiating the object with an X-ray dose from the X-ray source located at a plurality of steps along the arc shaped path, detecting the X-rays transmitted through the object with a stationary electronic X-ray detector, and constructing a three dimensional image of the object from a signal output by the electronic X-ray detector.

BRIEF DESCRIPTION OF THE DRAWINGS

FIGS. 10, 12 and 13 are three dimensional views of systems according to the fourth preferred embodiment of the invention.

DETAILED DESCRIPTION OF THE INVENTION

Figure 1:
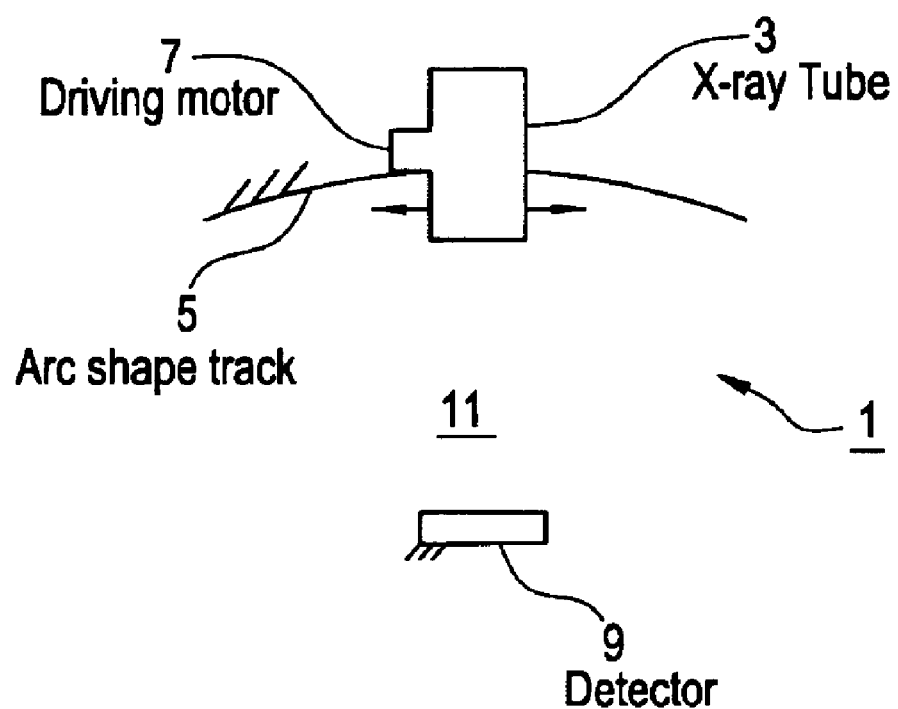
FIG. 1 is schematic illustration of a system according to the first preferred embodiment of the invention.

The present inventors have discovered that X-ray tomosynthesis imaging system speed and accuracy can be improved by using a track and a mechanical drive system which can position an X-ray source at any angle between the vertical to horizontal position on an arc shaped path. The track reduces the vibration of the X-ray source and reduces the driving power required to move the X-ray source.

The X-ray source is moved in a stepped motion (i.e., in a sequence of angle increments) about an arc shaped path by the mechanical driving mechanism at a high rate (about 0.1–1.5 seconds per step). The arc shaped path is a path that comprises a portion of a circle or a curved line. While less preferred, the path of the X-ray source may include a full circle, ellipse or polygon. A stationary electronic detector (i.e., an electronic device which detects X-rays, rather than an X-ray sensitive film) is used to detect the X-rays emitted by the X-ray source and attenuated by the imaged object.

The imaging system also contains an image processor, such as a general or special purpose computer or a microprocessor chip, such as an ASIC chip. The processor is electrically connected to the electronic detector. The processor forms a three dimensional image of an imaged object from a signal output by the electronic X-ray detector. The processor may use any suitable algorithm to reconstruct a three dimensional image of an imaged object from an arc shaped X-ray source scan. For example, such an algorithm is disclosed in related U.S. Pat. No. 6,707,878, to Jeffrey Eberhard and Bernhard Claus titled "Generalized Filtered Back-Projection Reconstruction In Digital Tomosynthesis" filed on the same date as the present application and incorporated herein by reference in its entirety. While less preferred, the method disclosed in U.S. Pat. No. 5,872,828, incorporated herein by reference in its entirety, may also be used. If desired, the processor may also be used to control the mechanical driving mechanism motion. Alternatively, a separate controller, such as a computer, microprocessor chip or a motor controller, may be used to control the mechanical driving mechanism motion. In this case, the controller is synchronized with the image processor.

The X-ray imaging system of the preferred embodiments may use any X-ray source, such as an X-ray tube. The X-ray source adapted to move in an arc shaped path is mounted onto a first support. The first support may have many different configurations, as will be described with respect to the preferred embodiments below. In some preferred embodiments the mechanical driving mechanism is adapted to move both the X-ray source and the first support in the arc shaped path. However, in other embodiments, the first support is not moved with the X-ray source.

Preferably, the electronic detector is mounted to a second support, such as a second support arm, which may be a substantially flat rectangular plate, a cylindrical tube or any other desired shape. An imaging volume is formed between the detector and the X-ray source. For example, an object to be imaged, such as a patient's breast, may be placed on the detector to be imaged and then the X-ray emitting X-ray source is rotated about the object to generate an image. The electronic detector may comprise any detector X-ray detector other than X-ray sensitive film. Preferably, the electronic detector comprises an X-ray sensitive scintillator which emits visible, UV or IR radiation and a solid state radiation detector, such as a silicon charge coupled device or an avalanche photodiode/transistor array, which converts the radiation into an electrical pulse to be sent to the processor. Other detectors, such as photomultipliers and direct X-ray to digital signal detectors, may alternatively be used if desired.

Preferably, the mammography system is positioned substantially vertical relative to ground (i.e., within 20 degrees of a plane perpendicular to the floor of the building that the system is mounted on), such that a patient standing adjacent to the system may place her breast onto the detector to be imaged. However, the system may also be positioned horizontally to image body parts of patients that are lying down, sitting or in any other desired position between vertical and horizontal. For example, if desired, the entire system may be manually or automatically positioned in any position from vertical to horizontal depending on the desired image.

The preferred system configurations of the preferred embodiments are described below. However, these configurations are merely illustrative and should not be considered limiting on the scope of the invention. Like part numbers in different figures are used to denote the same element.

The system 1 of the first preferred embodiment is schematically illustrated in FIG. 1. The system 1 includes an X-ray source 3, such as an X-ray tube. The X-ray source 3 is mounted on the first support, which in the first embodiment comprises an arc shaped track 5. The mechanical driving mechanism of the first embodiment comprises a motor 7. The motor 7 is attached to the X-ray source 3 and is adapted to move the X-ray source along the arc shaped track. The motor 7 is also preferably attached to the track 5. The electronic detector 9 is located facing the X-ray source 3 such that an imaging area 11 is formed above the electronic detector 9.

Figure 2:
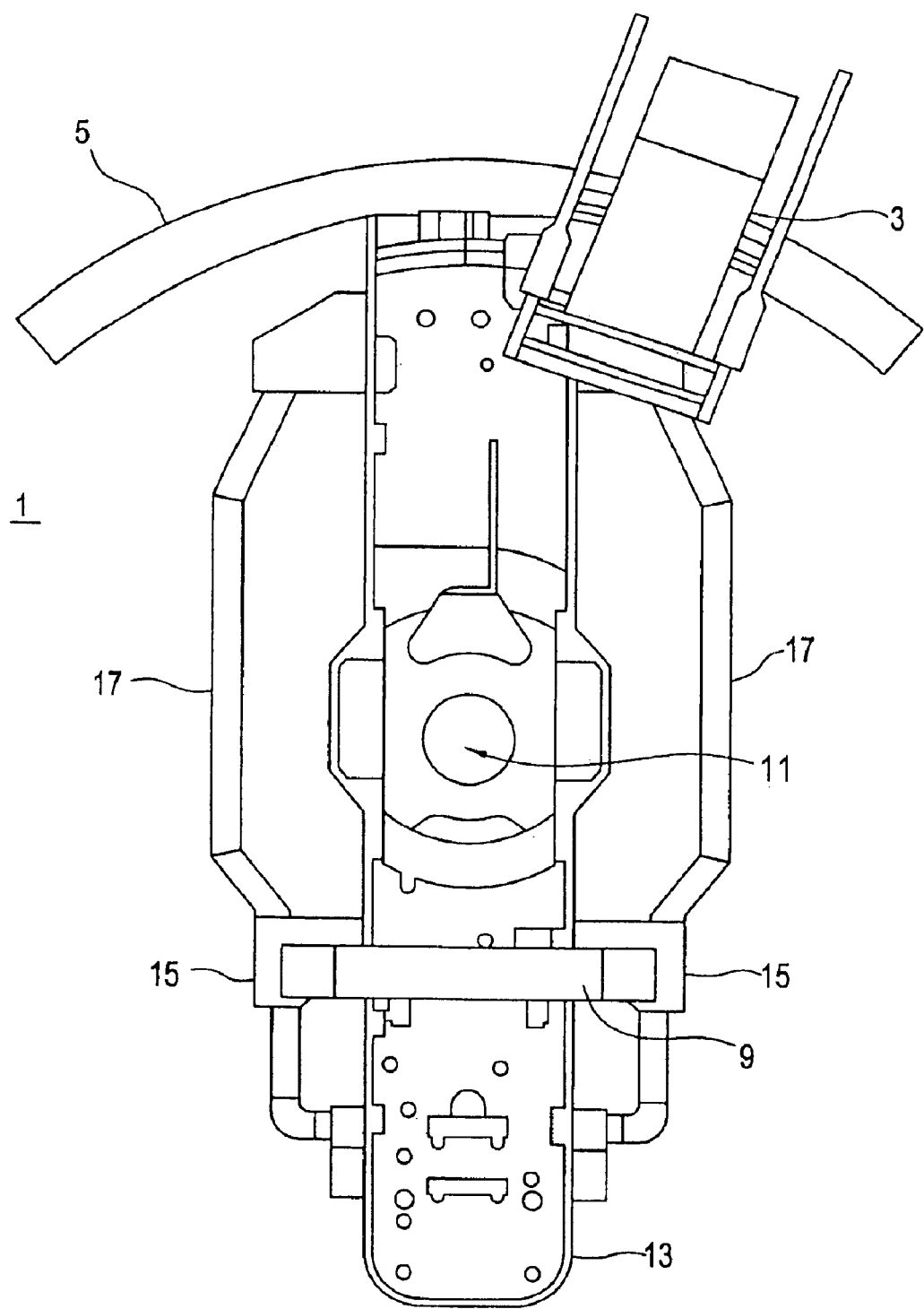
FIG. 2 is a side view of a system according to the first preferred embodiment of the invention.

FIG. 2 illustrates a preferred configuration of the system 1 shown in schematic form in FIG. 1. The arc shaped track 5 supports the X-ray tube 3. The motor 7 is not shown for clarity. As shown in FIG. 2, the detector 9 is mounted on a second support, which is a substantially rectangular, plate shaped arm 13, by fasteners 15, such as brackets, clamps, bolts and/or adhesive. The imaging area 11 optionally contains a breast compression paddle which is used to compress the patient's breast during imaging. The system also has optional handles 17, which may be used to tilt and/or move the system into a desired position. The remaining features on arm 13 shown in FIG. 2 comprise structural protrusions, recesses and mounting bolts.

Figure 3:
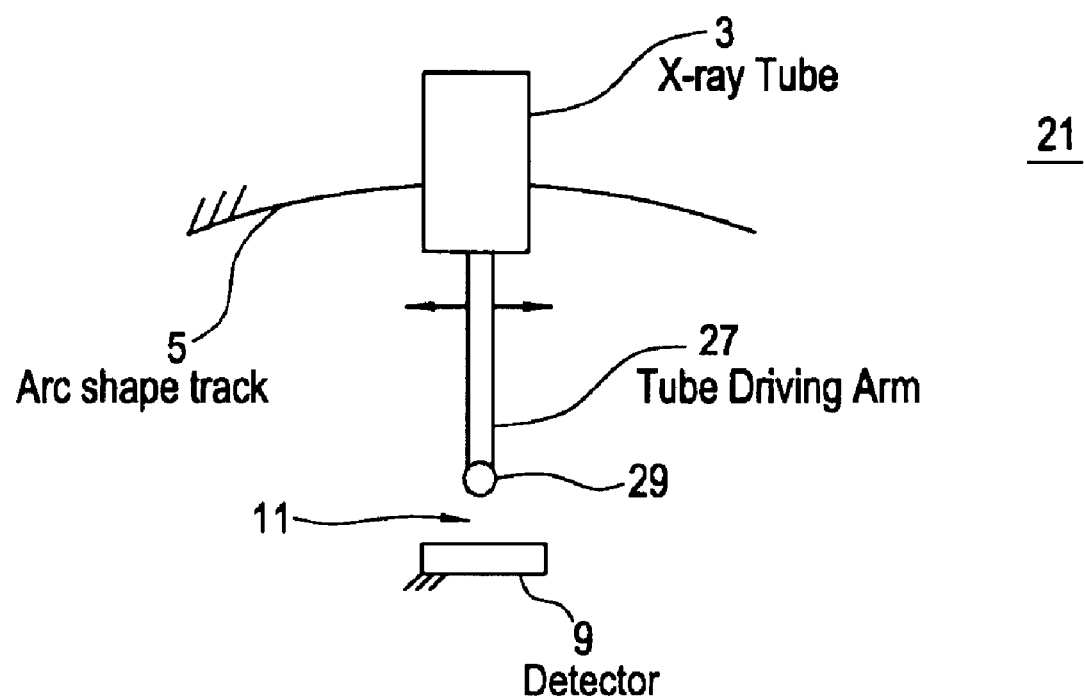
FIG. 3 is schematic illustration of a system according to the second preferred embodiment of the invention.

The system 21 of the second preferred embodiment is schematically illustrated in FIG. 3. The system 21 also includes an X-ray source 3 such as an X-ray lube. The X-ray source 3 is mounted on the first support, which in the second embodiment also comprises an arc shaped track 5. The mechanical driving mechanism of the first embodiment comprises a first arm 27. Preferably, the first arm 27 is made relatively thin and light weight to minimize its mass, but has sufficient rigidity to move the X-ray source 3 along the track 5. The first arm 27 may comprise a cylindrical or a plate shaped arm which connects the X-ray source 3 to a shaft 29. As shown in FIG. 3 the shaft 29 extends in and out of the page. The shaft 29 is turned by a motor or other rotation imparting device (not shown). The step motion of the X-ray source 3 is produced from the shaft 29 torque through the arm 27. The electronic detector 9 is located facing the X-ray source 3 such that an imaging area 11 is formed above the electronic detector 9.

The magnitude of dynamic forces resulting from the movement of parts in the systems 1 and 21 is linearly proportional to the motion acceleration and the mass in motion. The configurations of the first and second preferred embodiments are advantageous because they minimize the mass in motion. Only the X-ray source 3 alone, or the X-ray source and light weight arm 27 are moving along a track 5. This reduces the required driving power, which in turn allows a use of a motor with a lower weight and size. Since the X-ray source 3 moves along the track 5, its motion is precisely controlled by the track. This reduces the system vibration and improves the image quality. Furthermore, the center of the arc shaped path could be at the detector 9 location (such as in the first embodiment) or at the shaft 29 center (such as in the second embodiment) for optimization of the field of view.

Figure 4:
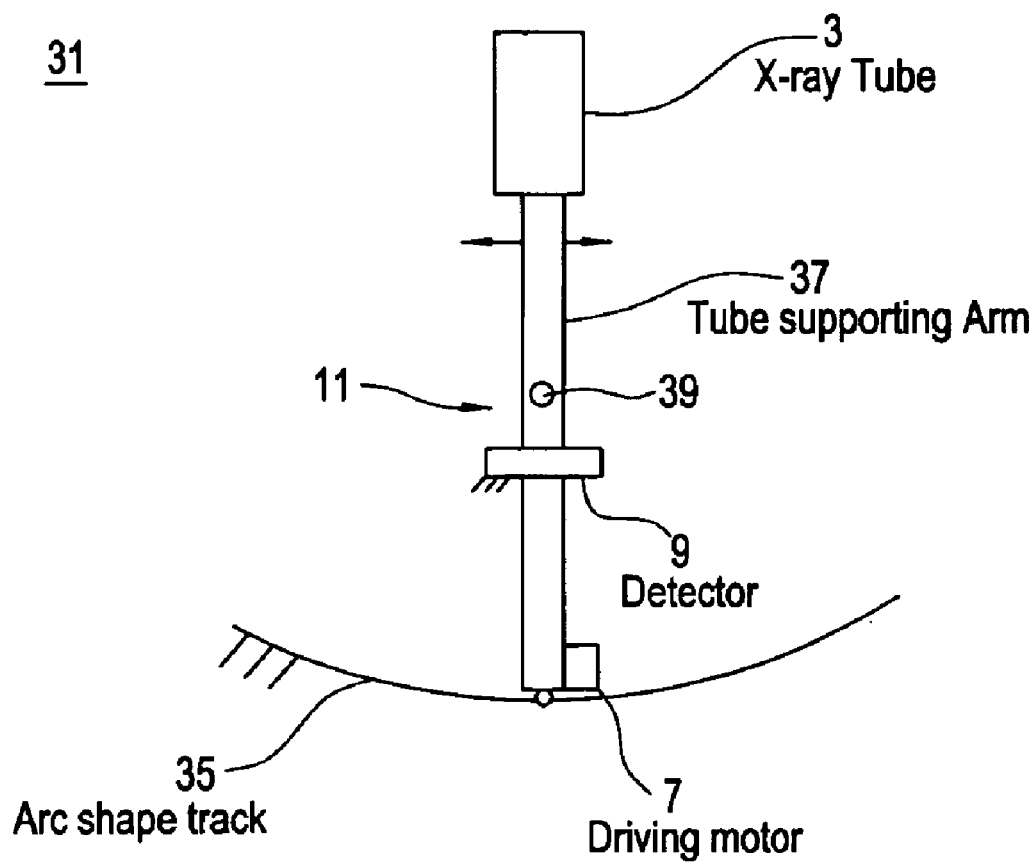
FIG. 4 is schematic illustration of a system according to the third preferred embodiment of the invention.

The system 31 of the third preferred embodiment is schematically illustrated in FIG. 4. In the third preferred embodiment, the X-ray source is supported by a rotational arm, which moves along an arc shaped track, rather than being supported by the track as in the first and second embodiment. Thus, the first support for the X-ray source 3 comprises a first arm 37. The arm 37 may have any desired shape, such as a tube or plate shape. The X-ray source 3 is mounted to an upper or first portion of the first arm 37. A lower or second portion of the first arm distal from the first portion is mounted to the arc shaped track 35.

The mechanical driving mechanism in this embodiment comprises a motor 7. The motor 7 is adapted to move the lower portion of the first arm 37 along the arc shaped track 35 to move the X-ray source 3 in the arc shaped path. The motor 7 may also be mounted onto the track if desired.

Figure 5:
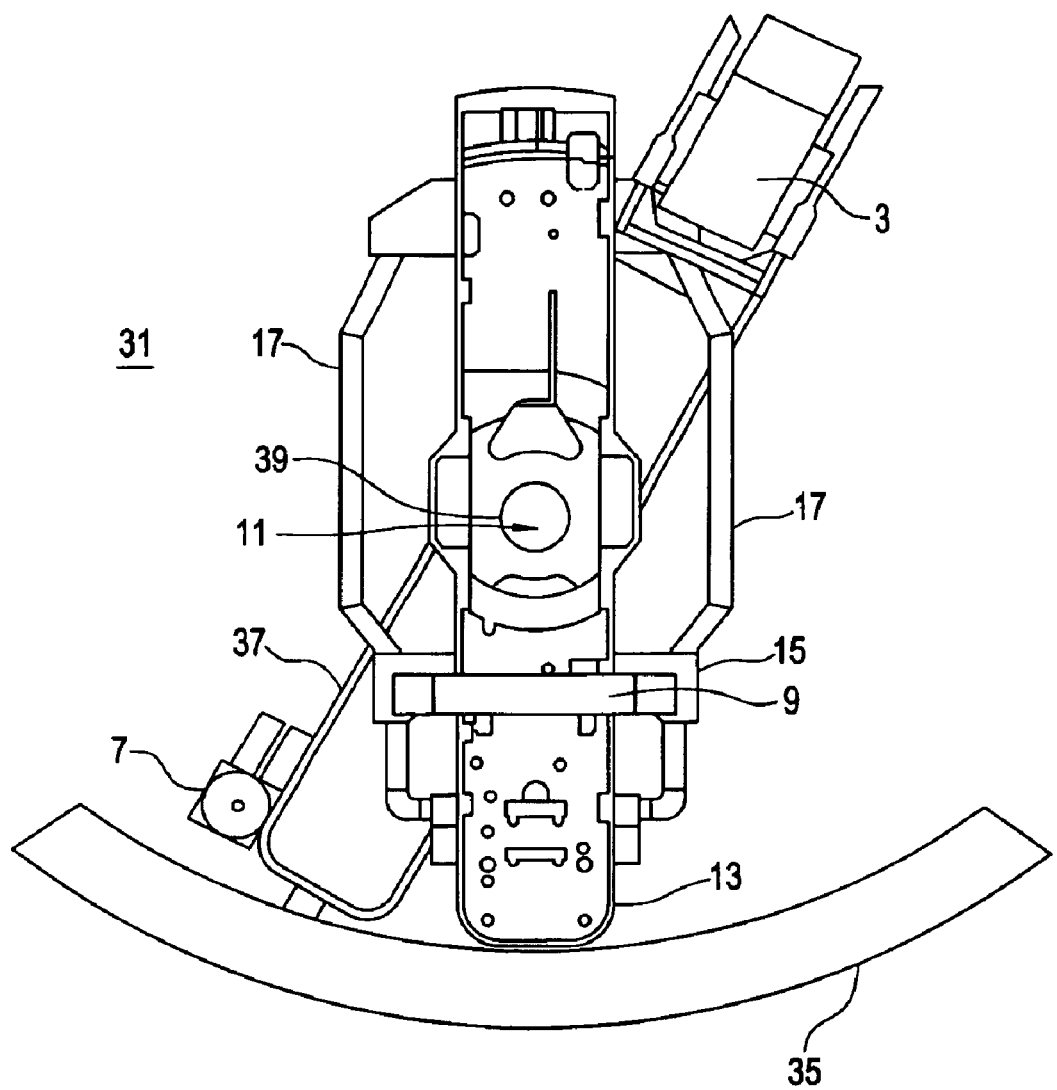
FIG. 5 is a side view of a system according to the third preferred embodiment of the invention.

FIG. 5 illustrates a preferred configuration of the system 31 shown in schematic form in FIG. 4. With reference to FIGS. 4 and 5, the detector 9 is mounted to a second support or arm 13, as in the first and second embodiments. A shaft 39 connects the middle portions of the first arm 37 and the second arm 13, such that the arms 13, 37 may rotate relative to each other about the shaft 39 in a scissors-like motion. Preferably, the second arm 13 is stationary while the first arm 37 rotates.

The electronic detector 9 is mounted to a first or front side of the plate shaped second arm 13, as shown in FIG. 5. The detector 9 faces the X-ray source 3 such that an imaging area 11 is formed above the electronic detector 9. The X-ray source 3 is mounted to the first arm 37 such that it is positioned adjacent to the front side of the second arm 13. Thus, the X-ray source 3 moves in the arc shaped path in a plane parallel to the front side of the second arm. However, the first arm 37 itself is preferably positioned adjacent to the second or back side of the second arm 13. A connector (not shown in FIG. 5 for clarity) connects the upper portion of the X-ray source 3 to the upper portion of first arm 37, such that the X-ray source 3 and the first arm move on the opposite sides of the second arm 13. Of course different configurations of the arms 13, 37 may be used if desired.

When the first arm 37 is rotating about the shaft 39, the X-ray source 3 is positioned for angular scans. The rotation torque is created by applying tangential force on the first arm 37 at a radial distance. The bigger the radial distance, the smaller the force is required for the same resultant torque. The lower end of the first arm 37 is the preferred location for the application of the torque because it is the location with the longest radial distance. Therefore, the driving power is minimized when the driving motor 7 is attached at the arm 37 end opposite to the X-ray source 3. The arc shaped track 35 defines the boundary of the first arm 37 motion. Thus, the outline of the moving parts is minimized because no additional moving parts are needed to drive the arm 37.

A shield or cover (not shown for clarity) is used to close the moving parts for safety reasons, with the X-rays being emitted through a small slit in the shield. The detector preferably protrudes from the shield. Since the system 31 is compact, the size of shield will be relatively small. This reduces the weight of the system which increases the system's natural frequencies to reduce system vibration.

Figure 6:
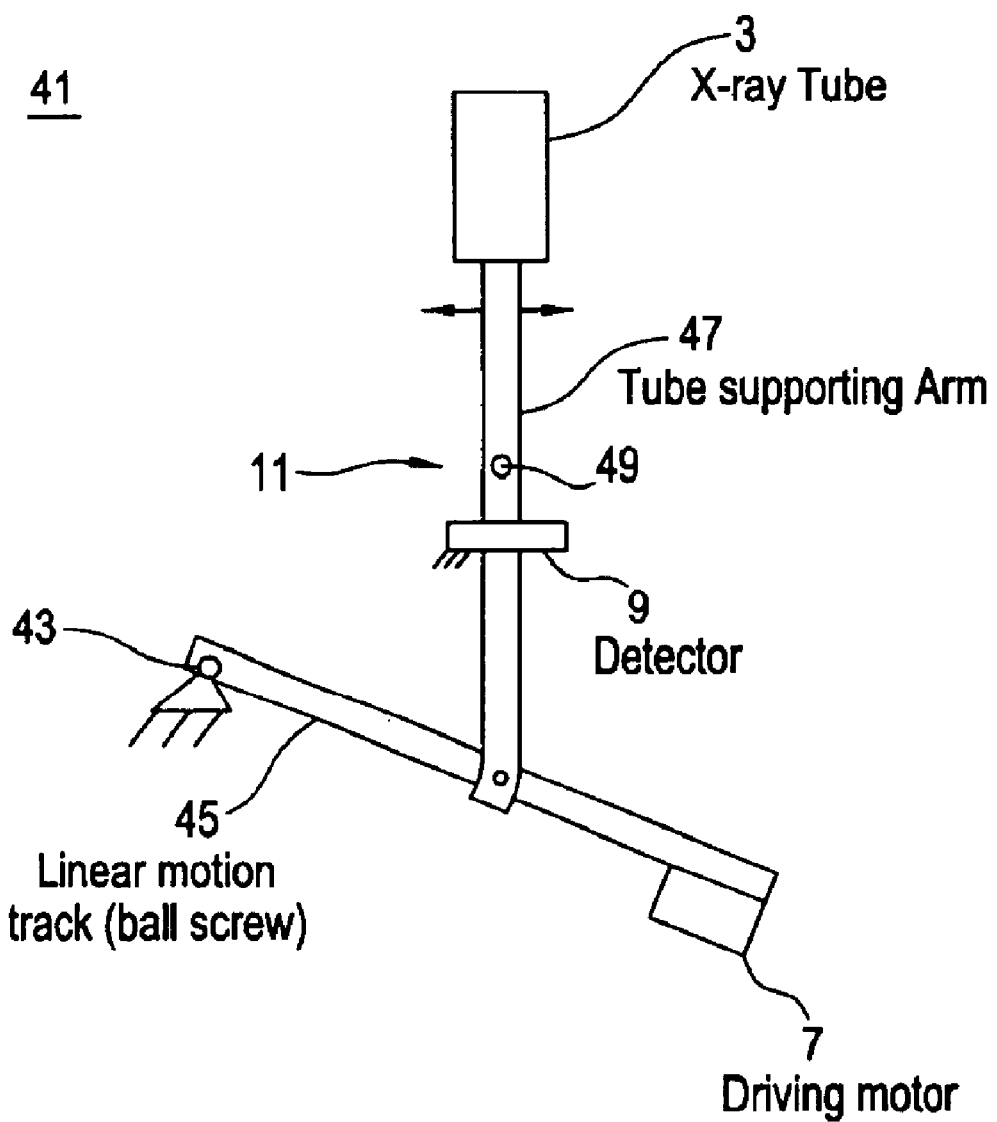
FIG. 6 is schematic illustration of a system according to the fourth preferred embodiment of the invention.

The system 41 of the fourth preferred embodiment is schematically illustrated in FIG. 6. The system 41 of the fourth preferred embodiment differs from the system 31 of the third preferred embodiment in that a linear motion track rather than an arc shaped track is used. The X-ray source 3 is mounted to an upper or first portion of the first arm 47. The first arm 47 may have any desired shape, such as a tube or plate shape. A lower or second portion of the first arm 47 distal from the first portion is mounted to the linear motion track 45.

The mechanical driving mechanism in this embodiment comprises a ball screw (not shown in the figures because it is located in the track 45) driven by a motor 7. The ball screw and motor 7 combination is adapted to move the lower portion of the first arm 47 along the track 45, to move the X-ray source 3 in the arc shaped path. The motor 7 may also be mounted onto the track if desired. A side pin 43 is positioned to create a stable whole range drive by allowing the track to rotate with respect to a fixed point.

Figure 7:
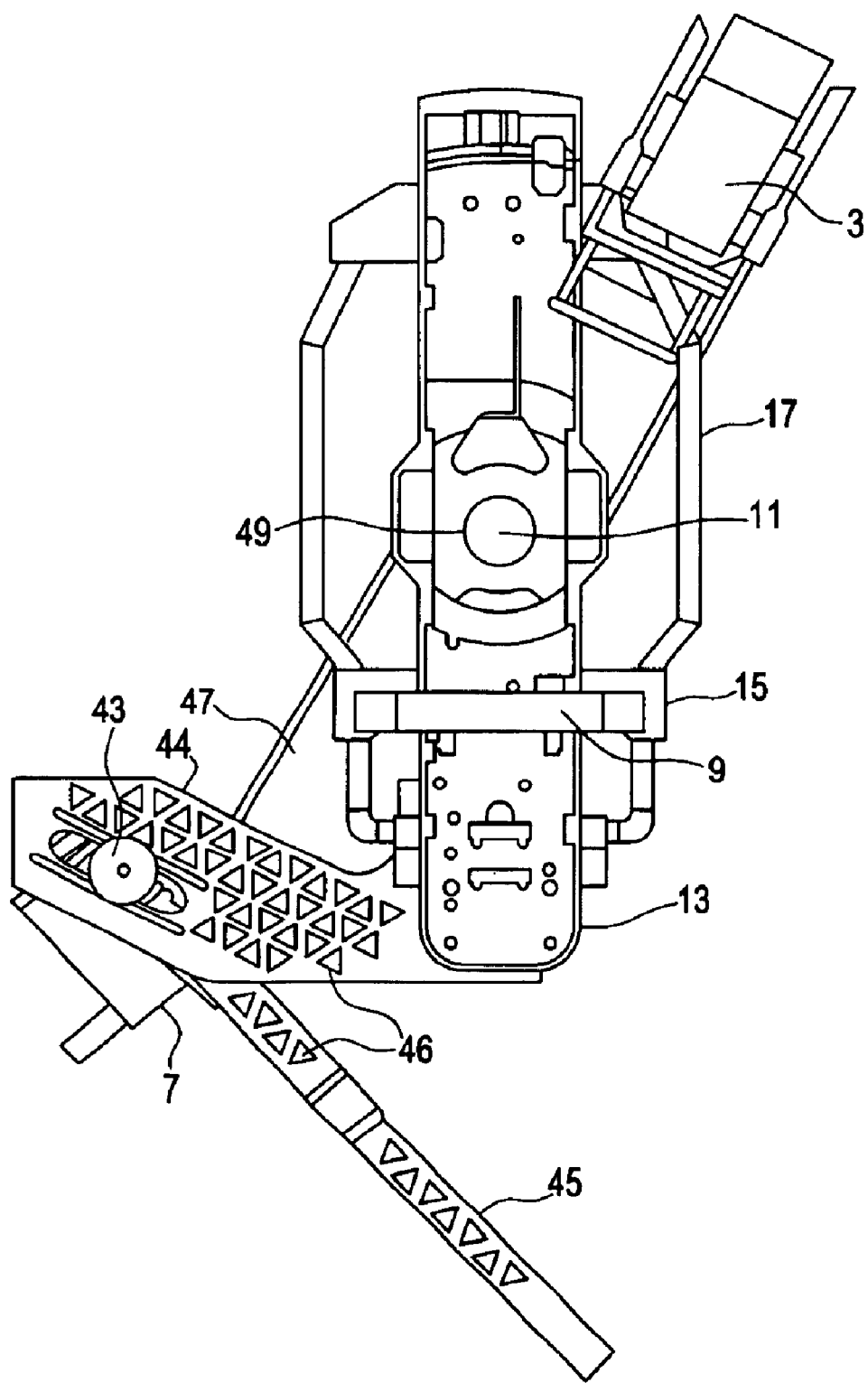
FIGS. 7–9 and 11 are side views of systems according to the fourth preferred embodiment of the invention.

FIG. 7 illustrates a preferred configuration of the system 41 shown in schematic form in FIG. 6. With reference to FIGS. 6 and 7, the detector 9 is mounted to a second support or arm 13, as in the first through third embodiments. A shaft 49 connects the middle portions of the first arm 47 and the second arm 13, such that the arms 13, 47 may rotate relative to each other about the shaft 49 in a scissors-like motion. Preferably, the second arm 13 is stationary while the first arm 47 rotates.

In a preferred embodiment of the fourth embodiment, a pivot point plate 44 is attached to the second arm 13, as shown in FIG. 7. The pivot point plate 44 is rotatably mounted to the linear motion track 45 by the side pin 43. The pivot plate 44 and track 45 optionally have holes 46 which reduce the weight of the plate 44 and track 45.

Figure 8:
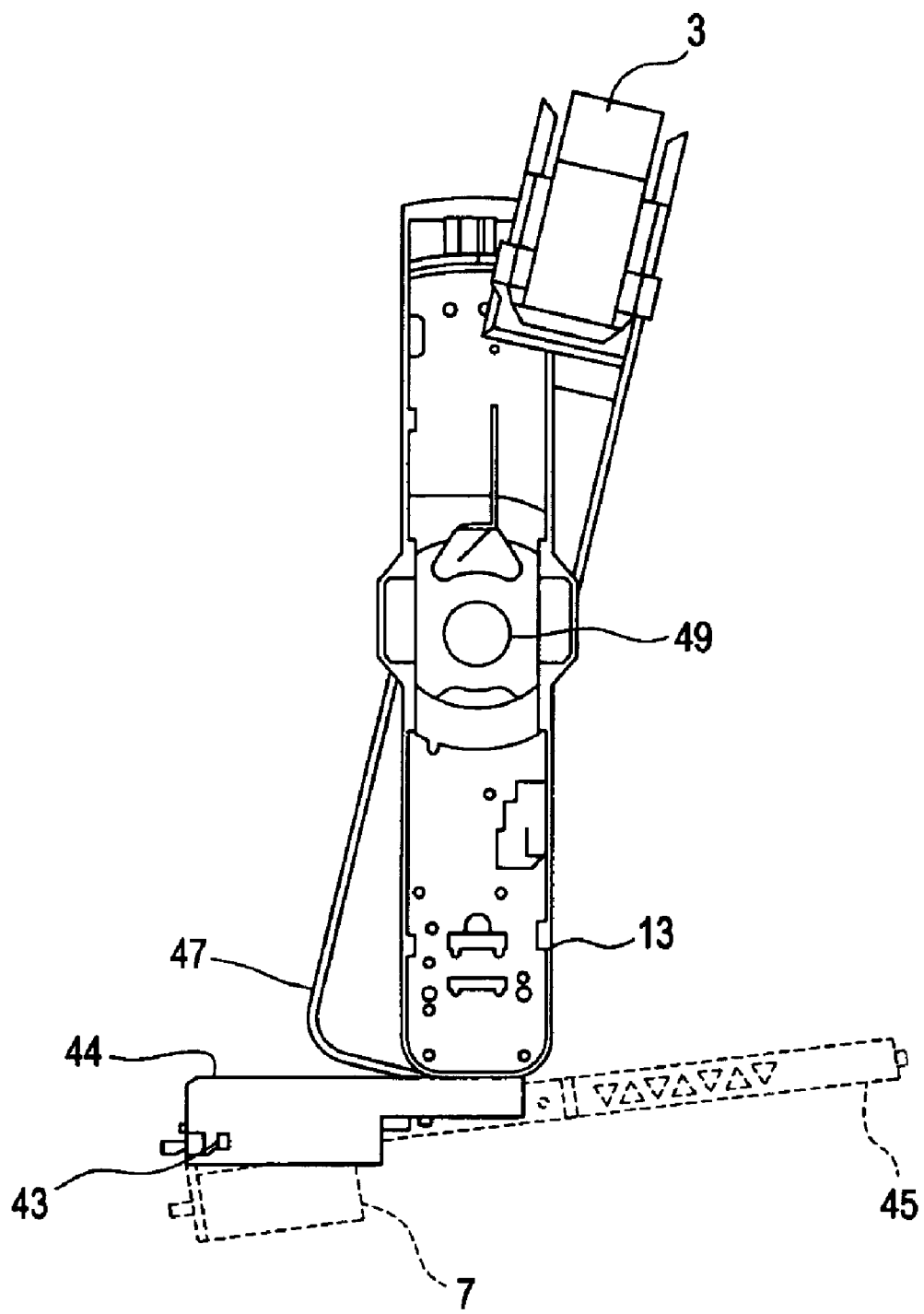
Figure 9:
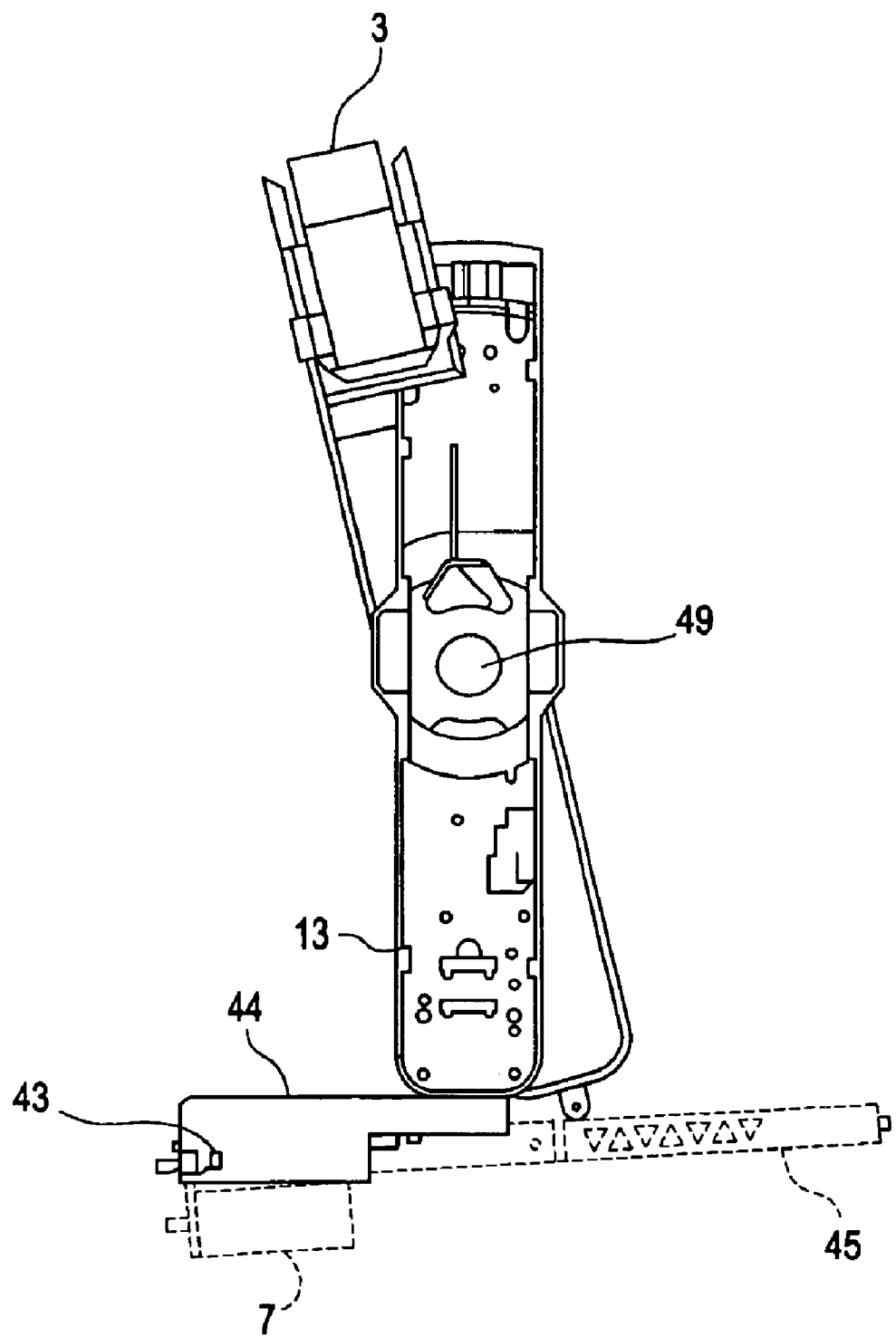

FIGS. 8 and 9 illustrate the method of operation of the system 41 of the fourth preferred embodiment. The X-ray source 3 is mounted to the first arm 47 such that it is positioned adjacent to the front side of the second arm 13. Thus, the X-ray source 3 moves in the arc shaped path in a plane parallel to the front side of the second arm. However, the first arm 47 itself is preferably positioned adjacent to the second or side of the second arm 13. A connector (not shown in FIGS. 8 and 9 for clarity) connects the upper portion of the X-ray source 3 to the upper portion of first arm 47, such that the X-ray source 3 and the first arm 47 may be moved past the second arm 13 on the opposite sides of arm 13. Of course different configurations of the arms 13, 47 may be used if desired.

The relative rotational movement of pivot plate 44 and track 45 around pin 43 allows movement of the first arm 47 relative to track 45. Preferably, the second arm 13 supporting the detector 9 remains stationary while the track 45 moves relative to the second arm. The first arm 47 and the second arm 13 are rotatably connected by shaft 49. The movement of the track 45 relative to second arm 13 allows translation of the linear motion of the lower portion of the first arm 47 along track 45 into arc shaped motion of the X-ray source 3 mounted to the upper portion of the first arm 47, as shown in FIGS. 8 and 9. The X-ray source 3 moves from a right side position in FIG. 8 along the arc shaped path into a left side position relative to the second arm 13 in FIG. 9. At the same time, the track 45 moves from an first position in FIG. 8 to a second position in FIG. 9 relative to the second arm 13, while the lower portion of the first 47 moves from left in FIG. 8 to right in FIG. 9 to achieve the arc shaped path of the X-ray source 3. Thus, the track 45 moves vertically relative to the shaft 49 during movement of the first arm 47 to translate linear motion along track 45 into arc shaped motion.

Figure 10:
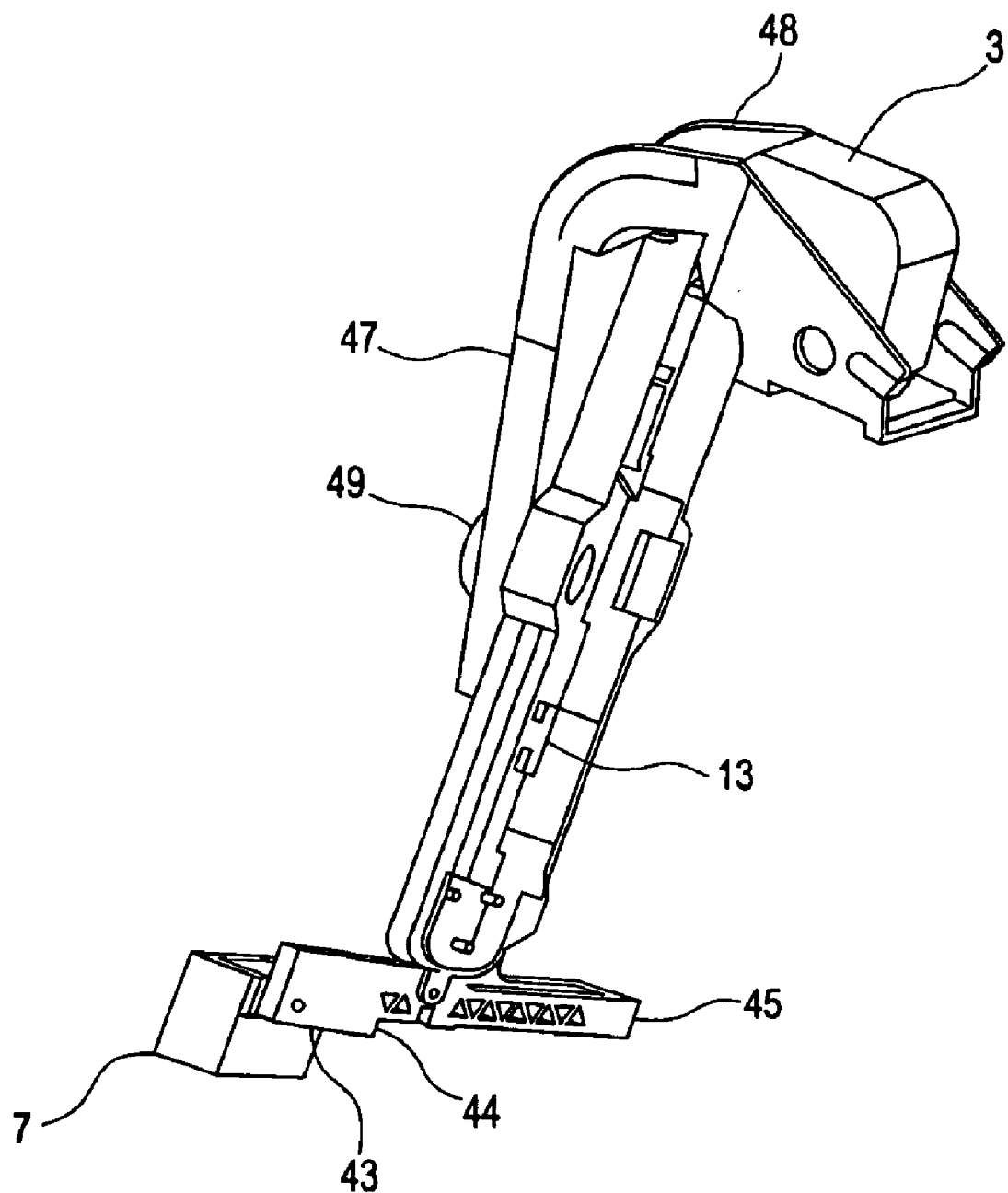

FIG. 10 is a three dimensional illustration of system 41 of the fourth preferred embodiment. FIG. 10 shows the connector 48 which connects the first arm 47 and the X-ray source 3. The connector 48 extends over the second arm 13 and allows the first arm 47 and the X-ray source 3 to move on opposite sides of the second arm 13.

Figure 11:
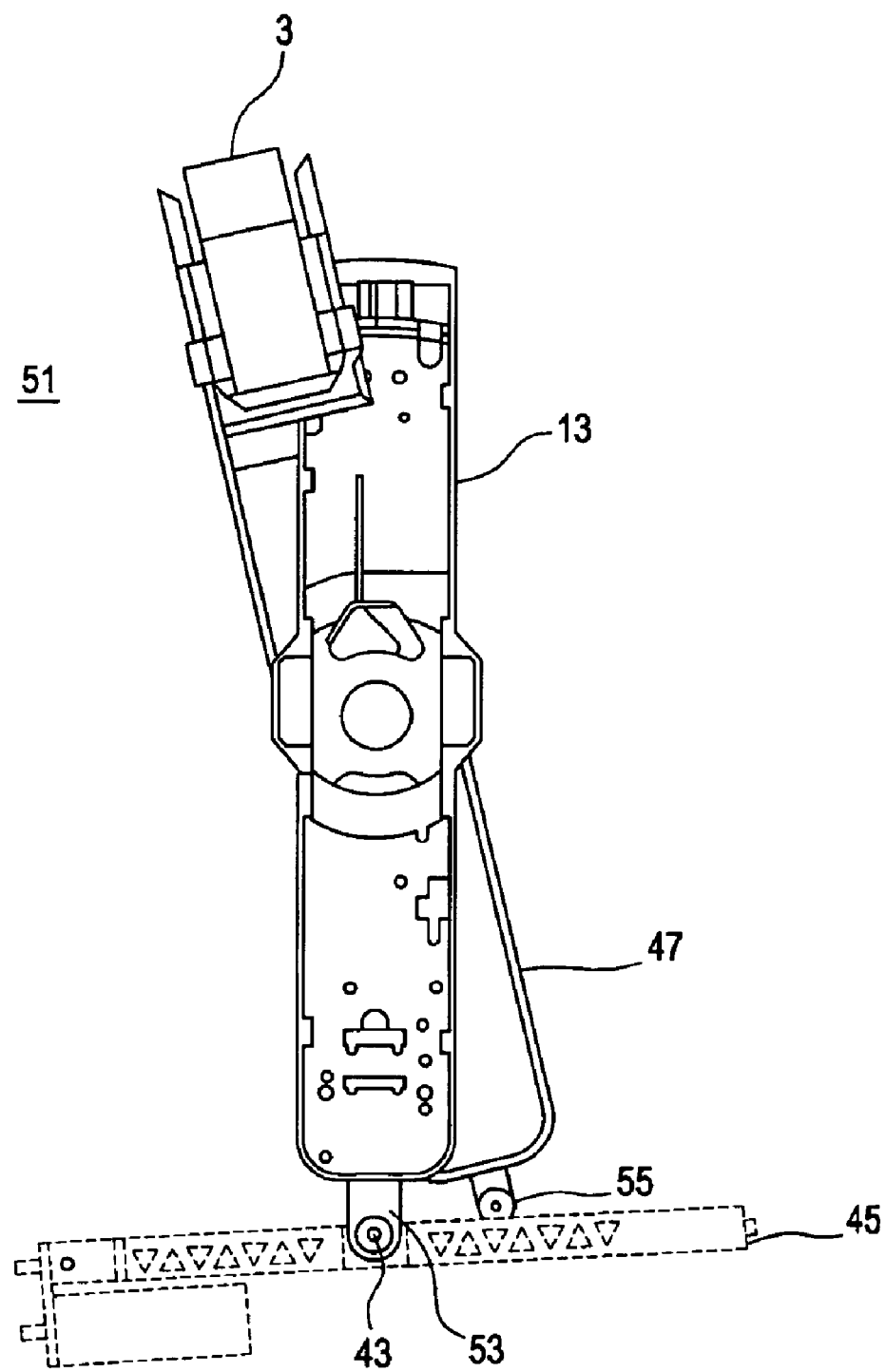
Figure 12:
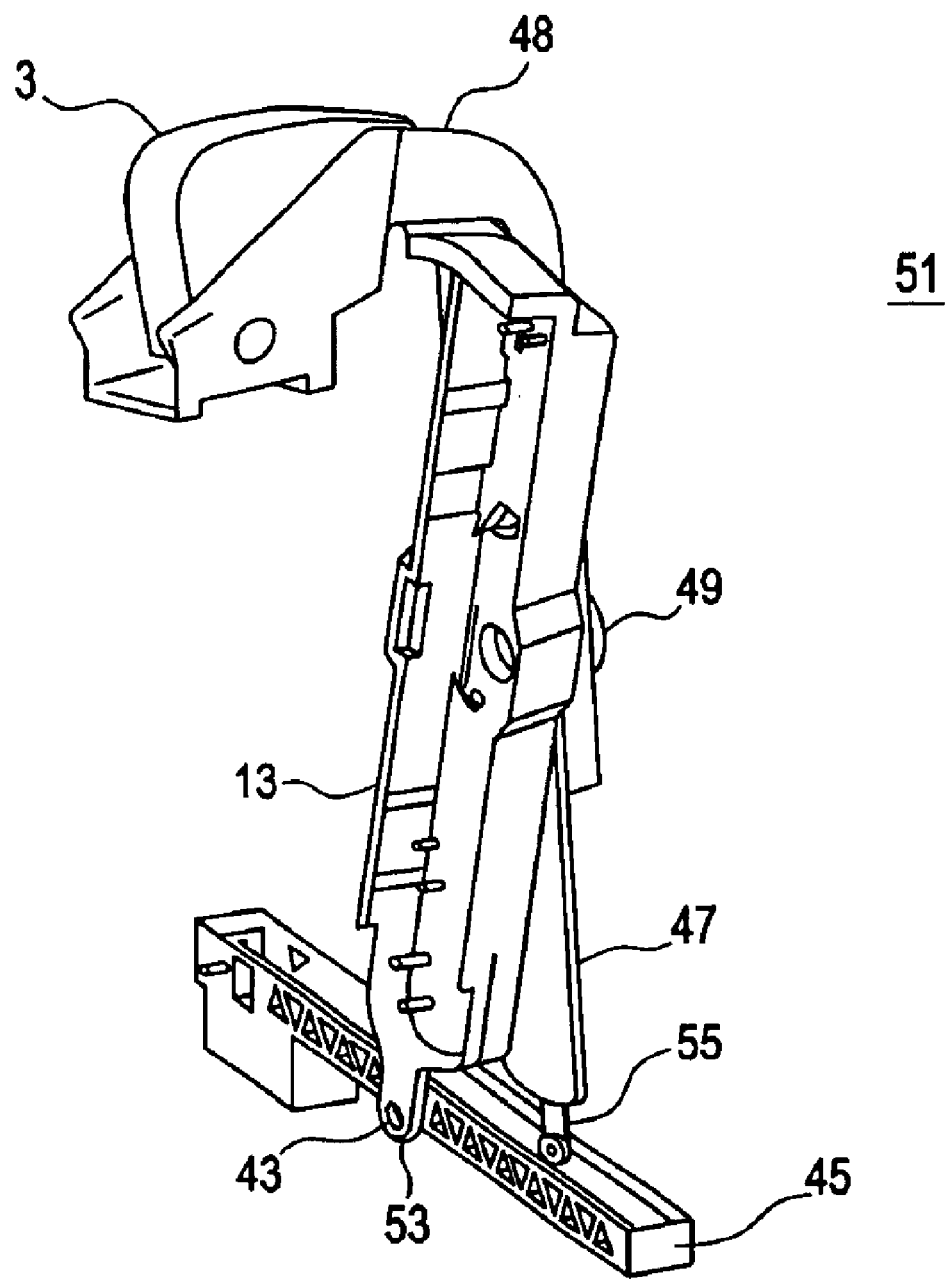

FIGS. 11 and 12 illustrate an alternative aspect of the system of the fourth preferred embodiment. In this aspect, the pivot plate 44 is omitted from the system 51. Instead, the second arm 13 is mounted to the track 45 by a movable member 53 and pin 43. The movable member allows relative vertical motion between the second arm 13 and the track 45. For example, the movable member 53 may be a piston which is rotatably mounted to the track 45 by pin 43, and which extends and retracts in a direction perpendicular to the track 45 to allow the relative movement between the secondary arm 13 and the track 45. This motion allows the X-ray source 3 to move in the arc shaped path. The first arm 47 is connected to the track 45 by a pin 55 which allows rotational movement of arm 47 relative to track 45 as well as linear motion of arm 47 along the track 45.

FIG. 13 illustrates the system 41 of the fourth preferred embodiment mounted to a gantry or base 57. The right side of FIG. 13 shows a close up of the first arm 47 and the second arm 13, while the left side of FIG. 13 shows a close up of the electronic detector 9. The detector 9 is mounted over the gantry 57 in a position which allows a patient to place her breast onto the detector 9. The system 41 may be adjustable in the vertical direction relative to the ground to allow patients of different height to use the system without stretching or bending. The compression paddle 58 is likewise height adjustable. The preferred electronic detector 9 contains an amorphous silicon photodetector array 61 formed on a glass substrate 59. The array 61 includes metal contact fingers 63 and metal contact leads 65. An X-ray sensitive scintillator material 67 is formed over the array 61. The scintillator material 67 emits radiation having a wavelength detectable by the silicon pixels in the array 61 in response to receiving an X-ray. The magnitude of the radiation is proportional to the attenuation of the X-rays by the imaged object. The pixels of array 61 converts the received radiation into an electrical signal of a predetermined magnitude that is provided to the processor and then converted into an image by the processor.

It should be noted that "upper" and "lower" refers to directions in a preferred vertically mounted system. These directions would differ in a non-vertically mounted system of other aspects of the present invention. The mechanical driving system of the preferred embodiments requires low driving power, provides a low amount of system vibration, and a small outline of moving part boundary to reduce the size of the system. The X-ray tomosynthesis imaging system with the track, the mechanical drive and electronic detector is especially advantageous for mammography because it forms an accurate three dimensional image of the breast in a short amount of time and provides an improved image contrast adjacent to the skin of the breast. However, the imaging system may be used to image other parts of a patient's body as well as animals and inanimate objects, if desired.

As discussed above, the systems of the preferred embodiments of the present invention are preferably used in a tomosynthesis X-ray mammography imaging method. However, other patient body parts, animals and/or inanimate objects may also be imaged if desired. The preferred mammography method includes mechanically moving the X-ray source 3 in a stepped motion on an arc shaped path around a patient's breast and irradiating the patient's breast with an X-ray dose from the X-ray source located at a plurality of steps along the arc shaped path. The X-rays transmitted through the patient's breast are then detected with the electronic X-ray detector 9 and a three dimensional image of the patient's breast is constructed from a signal output by the electronic X-ray detector 9. Preferably, the detector 9 is arranged at the gantry 57 such that the patient is standing adjacent to the machine and the patient's breast is located on the electronic X-ray detector 9, while the X-ray source 3 moves above the patient's breast in the arc shaped path.

In the first preferred embodiment, the step of mechanically moving an X-ray source comprising moving the X-ray source 3 on the arc shaped track 5. In the second preferred embodiment, the X-ray source 3 is moved on the arc shaped track 5 by a first arm 27 being rotated by a motor. In the third preferred embodiment, the step of mechanically moving an X-ray source 3 comprises moving a first portion of a first arm 37 on the arc shaped track 35 while a second portion of the first arm 37 supports the X-ray source 3. In the fourth preferred embodiment, the step of mechanically moving an X-ray source comprises moving the first arm 47 supporting the X-ray source 3 on a linear motion track 45 while allowing relative motion between the track 45 and a second arm 13 supporting the electronic X-ray detector 9.

The method of the preferred embodiments of the present invention is advantageous because it allows for a fast scan of the imaged object. For example, 10 projections can be taken in about 1 to 15 seconds, such as 3 to 10 seconds, preferably 3 to 5 seconds. Thus, the X-ray source takes between 0.1 to 1.5 seconds between projection positions, such as 0.1 to 0.5 seconds or 0.3 to 1 seconds, preferably 0.3 to 0.5 seconds. The X-ray source 3 is capable of traveling an arc shaped path of 50 or more degrees, such as about 20 to 60, preferably 30 to 50 degrees, such that the arc shaped path contains 5 to 15 steps separated by about 2 to about 10 degrees. The X-ray source emits a dose of X-rays at each step. This provides for a fast patient throughput while maintaining accurate, repeatable, customizable, automated X-ray source motion. Furthermore, the electronic detector 9, such as a digital detector, is capable of handling multiple exposures per second, in contrast to conventional X-ray film.

The preferred embodiments have been set forth herein for the purpose of illustration. However, this description should not be deemed to be a limitation on the scope of the invention. Accordingly, various modifications, adaptations, and alternatives may occur to one skilled in the art without departing from the scope of the claimed inventive concept.

What is claimed is:

1. An imaging system, comprising:
   an X-ray source operable to move in an arc shaped path;
   a stationary electronic X-ray detector;
   an arc shaped track on which the X-ray source is mounted; and
   a mechanical driving mechanism operable to move the X-ray source in the arc shaped path, and comprising a first arm, having a first portion connected to the X-ray source and a second portion connected to a motor configured to provide torque to the second portion of the first arm to move the X-ray source alone the arc shaped track.

2. The system of claim 1, further comprising a processor electrically connected to the electronic X-ray detector, wherein the processor forms a three dimensional image of an imaged object from a signal output by the electronic X-ray detector.

3. The system of claim 2, wherein the electronic X-ray detector is mounted to a second support, such that an imaging volume is formed above the detector where a patient's breast is to be placed to be imaged.

4. The system of claim 3, wherein the electronic X-ray detector comprises an X-ray sensitive scintillator and a solid state radiation detector.

5. The system of claim 1, wherein:

the system is a tomosynthesis mammography system;

the system is positioned substantially vertical relative to ground; and the mechanical driving mechanism is operable to move the X-ray source in a stepped motion in the arc shaped path.

6. The system of claim 1, wherein:

the track comprises an arc shaped track;

the X-ray source is mounted to the arc shaped track; and the mechanical driving mechanism comprises a motor which is attached to the X-ray source and is configured to move the X-ray source along the arc shaped track.

7. A tomosynthesis X-ray mammography imaging system, comprising:

an X-ray source operable to move in an arc shaped path and connected to a first portion of a first arm;

an arc shaped track on which the X-ray source is mounted to allow the X-ray source to move in the arc shaped path;

a stationary electronic X-ray detector positioned opposite to the X-ray source; and mechanical driving mechanism operable to move the X-ray source in the arc shaped path, wherein a second portion of the first arm distal from the first portion is connected to the mechanical driving mechanism comprising a motor configured to rotate the second portion of the first arm to move the X-ray source along the arc shaped track.

8. The system of claim 7, further comprising a processor electrically connected to the electronic X-ray detector, wherein the processor forms a three dimensional image of an imaged object from a signal output by the electronic X-ray detector.

9. The system of claim 8, wherein:

the electronic detector is mounted to a detector support, such that an imaging volume is formed above the detector where a patient's breast is to be placed to be imaged;

the electronic X-ray detector comprises an X-ray sensitive scintillator and a solid state radiation detector; and the system is positioned substantially vertical relative to ground.

10. The system of claim 7, wherein:

the X-ray source is mounted to the arc shaped track;

the mechanical driving mechanism comprises a motor which is attached to the X-ray source and is configured to move the X-ray source along the arc shaped track; and the electronic X-ray detector is located facing the X-ray source such that an imaging volume is formed above the electronic X-ray detector.

11. A tomosynthesis X-ray imaging system, comprising:

an X-ray source mounted onto an upper portion of a first arm;

a second arm having a first side and a second side, a stationary electronic X-ray detector mounted facing the X-ray source to the first side of the second arm such that an imaging volume is formed above the electronic X-ray detector;

a shaft rotatably connecting a middle portion of the first arm to a middle portion of the second side of the second arm;

a linear motion track operable to move relative to the second arm; and a mechanical driving mechanism operable to move a lower portion of the first arm along the linear motion track such that the X-ray source moves in an arc shaped path.

12. The system of claim 11, further comprising:

a processor electrically connected to the electronic X-ray detector, wherein the processor forms a three dimensional image of an imaged object from a signal output by the electronic X-ray detector;

a pivot plate connected to a lower portion of the second arm; and a pivot pin rotatably connecting the pivot plate to the linear motion track, such that the linear motion track moves relative to the second arm while the X-ray source moves in the arc shaped path.

13. The system of claim 12, wherein:

the X-ray source is mounted to the first arm such that it is positioned adjacent to the first side of the second arm and moves in the arc shaped path in a plane parallel to the first side of the second arm;

the electronic detector comprises an X-ray sensitive scintillator and a solid state X-ray radiation detector;

the mechanical driving mechanism comprises a ball screw; and the system is positioned substantially vertical relative to ground.

14. The system of claim 11, further comprising:

a processor electrically connected to the electronic X-ray detector, wherein the processor forms a three dimensional image of an imaged object from a signal output by the electronic X-ray detector;

a movable member connected to a lower portion of the second arm; and a pivot pin rotatably connecting the movable member to the linear motion track, such that the length of the movable member varies as the linear motion track moves relative to the second arm while the X-ray source moves in the arc shaped path.

15. A tomosynthesis X-ray mammography imaging system, comprising:

a first means for irradiating a patient's breast with an X-ray dose at plurality of steps along an arc shaped path;

a second means for mechanically moving the first means in a stepped motion on the arc shaped path around the patient's breast including an arm displaced in rotation by a drive motor using a track;

a third means for detecting the X-rays transmitted through the patient's breast; and a fourth means for constructing a three dimensional image of the patient's breast from a signal output by the third means.

16. The system of claim 15, wherein the system is positioned substantially vertical relative to ground.

17. The system of claim 15, further comprising a fifth means for providing the arc shaped path for the first means.

18. The system of claim 17, further comprising a sixth means for connecting the first means to the second means, and for moving the first means along the fifth means.

19. The system of claim 15, further comprising:
a seventh means for connecting the first means to the second means; and
an eighth means for providing an arc shaped path for movement of the seventh means.

20. The system of claim 15, further comprising:
a seventh means for connecting the first means to the second means;
an eighth means for providing a linear motion path for the seventh means;
a ninth means for supporting the third means such that an imaging volume is formed;
a tenth means for allowing relative motion between the eighth means and the ninth means to allow the first means to move in the arc shaped path while the seventh means moves along the linear motion path.

21. The system of claim 15, further comprising a ninth means for supporting the third means such that an imaging volume is formed.

22. A tomosynthesis X-ray imaging method, comprising:
mechanically moving an X-ray source by a first arm rotated by motor in a stepped motion on an arc shaped path around an object using a track;
irradiating the object with an X-ray dose from the X-ray source located at a plurality of steps along the arc shaped path;
detecting the X-rays transmitted through the object with a stationary electronic X-ray detector; and
constructing a three dimensional image of the object from a signal output by the electronic X-ray detector.

23. The method of claim 22, wherein the step of mechanically moving an X-ray source comprises moving a first portion of a first arm on arc shaped track while a second portion of the first arm supports the X-ray source.

24. The method of claim 22, wherein the step of mechanically moving an X-ray source comprises moving a first arm supporting the X-ray source on a linear motion track while allowing relative motion between the track and second arm supporting electronic X-ray detector.

25. The method of claim 22, wherein:
the object comprises a patient's breast;
the patient is standing adjacent to the machine;
the patient's breast is located on the electronic X-ray detector; and
the X-ray source moves above the patient's breast in the arc shaped path.

26. The method of claim 25, wherein the X-ray source moves in the stepped motion at a speed of about 0.1 to about 1.5 seconds per step long the arc shaped path of about 20 to about 60 degrees.

27. The method of claim 26, wherein:
the arc shaped path contains 5 to 15 steps separated by about 2 to about 10 degrees; and
the X-ray source emits a dose of X-rays at each step.

28. An imaging system, comprising:
an X-ray source mounted to a first portion of a first arm and operable to move in an arc shaped path;
a stationary electronic X-ray detector;
an arc shaped track, wherein a second portion of the first arm distal from the first portion is mounted to the arc shaped track; and
a mechanical driving mechanism comprising a motor configured to move the second portion of the first arm along the arc shaped track to move the X-ray source in the arc shaped path.

29. The system of claim 28, wherein:
the electronic X-ray detector is mounted facing the X-ray source to a first side of a second arm such that an imaging volume is formed above the electronic X-ray detector;
a middle portion of the first arm is attached to a second side of the second arm; and
the X-ray source is mounted to the first arm such that it is positioned adjacent to the first side of the second arm and moves in the arc shaped path in a plane parallel to the first side of the second arm.

30. An imaging system, comprising:
an X-ray source mounted to a first portion of a first arm and operable to move in an arc shaped path;
a stationary electronic X-ray detector;
a linear motion track, wherein a second portion of the first arm distal from the first portion is mounted to the linear motion track; and
a mechanical driving mechanism comprising a ball screw configured to move the second portion of the first arm along the linear motion track to move the X-ray source in the arc shaped path.

31. The system of claim 30, wherein:
the stationary electronic X-ray detector is mounted facing the X-ray source to a first side of a second arm such that an imaging volume is formed above the stationary electronic X-ray detector;
a middle portion of the first arm is attached to a second side of the second arm; and
the X-ray source is mounted to the first arm such that it is position adjacent to the first side of the second arm and moves in the arc shaped path in a plane parallel to the first side of the second arm.

32. A tomosynthesis X-ray mammography imaging system, comprising:
an X-ray source mounted to a first portion of a first arm and operable to move in an arc shaped path;
an arc shaped track provided to allow the X-ray source to move in the arc shaped path, wherein a second portion of the first arm distal from the first portion is mounted to the arc shaped track;
a stationary electronic X-ray detector positioned opposite to the X-ray source; and
a mechanical driving mechanism comprising a motor configured to move the second portion of the first arm along the arc shaped track to move the X-ray source in the arc shaped path.

33. A tomosynthesis X-ray imaging method, comprising:
mechanically moving an X-ray source in a stepped motion on an arc shaped path around an object using a track by moving a first portion of a first arm on arc shaped track while a second portion of the first arm supports the X-ray source;
irradiating the object with an X-ray dose from the X-ray source located at a plurality of steps along the arc shaped path;
detecting the X-rays transmitted through the object with a stationary electronic X-ray detector; and
constructing a three dimensional image of the object from a signal output by the electronic X-ray detector.

34. A tomosynthesis X-ray imaging method, comprising:
mechanically moving an X-ray source in a stepped motion on an arc shaped path around an object using a track by moving a first arm supporting the X-ray source on a linear motion track while allowing relative motion between the track and second arm supporting an electronic X-ray detector;

irradiating the object with an X-ray dose from the X-ray source located at a plurality of steps along the arc shaped path;

detecting the X-rays transmitted through the object with the electronic X-ray detector; and constructing a three dimensional image of the object from a signal output by the electronic X-ray detector.

* * * * *

UNITED STATES PATENT AND TRADEMARK OFFICE
CERTIFICATE OF CORRECTION

PATENT NO. : 6,882,700 B2  Page 1 of 1
APPLICATION NO. : 10/063357
DATED : April 19, 2005
INVENTOR(S) : Yu Wang, Reinhold Franz Wirth and James Pellegrino Alexander It is certified that error appears in the above-identified patent and that said Letters Patent is hereby corrected as shown below:

In Claim 1, column 8, line 64, change "alone" to --along--.

In Claim 26, column 11, line 54, replace "long" with --along--.

Signed and Sealed this

Eighteenth Day of August, 2009

David J. Kappos
*Director of the United States Patent and Trademark Office*